(12) United States Patent
Srivastava et al.

(10) Patent No.: US 7,019,284 B2
(45) Date of Patent: Mar. 28, 2006

(54) ULTRAVIOLET EMITTING SCINTILLATORS FOR OIL DETECTION

(75) Inventors: Alok Mani Srivastava, Niskayuna, NY (US); Holly Ann Comanzo, Niskayuna, NY (US); Charles David Greskovich, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 280 days.

(21) Appl. No.: 10/617,643

(22) Filed: Jul. 11, 2003

(65) Prior Publication Data

US 2006/0027742 A1    Feb. 9, 2006

(51) Int. Cl.
   *G01V 5/04*    (2006.01)
(52) U.S. Cl. .................................................... 250/256
(58) Field of Classification Search ................. 250/256
   See application file for complete search history.

(56) References Cited

U.S. PATENT DOCUMENTS

| | | | | |
|---|---|---|---|---|
| 4,649,276 | A | * | 3/1987 | Suzuki ................. 250/370.11 |
| 5,483,062 | A | * | 1/1996 | Czirr et al. ................. 250/256 |
| 5,484,750 | A | | 1/1996 | Greskovich et al. |
| 5,581,087 | A | * | 12/1996 | Uddin et al. ........... 250/370.11 |
| 6,093,347 | A | | 7/2000 | Lynch et al. |
| 6,246,744 | B1 | | 6/2001 | Duclos et al. |
| 6,358,441 | B1 | | 3/2002 | Duclos et al. |
| 6,528,796 | B1 | * | 3/2003 | Kaifu et al. ........... 250/370.11 |

OTHER PUBLICATIONS

M. Nikl et al., "Photo- and radioluminescence of Pr-doped Lu3Al5O12 single crystal" phys. stst. sol. (a) vol. 202, No. 1, pp. R4-R6 (Jan. 2005).*
C.W.E. van Eijk et al., "Nd3+ and Pr 3+ Doped Inorganic Scintillators" IEEE Trans. Nuc. Sci., vol 41, No. 4, pp. 738-741 (Aug. 1994).*
P. Doenbos et al., "Scintillation properties of some Ce3+ and Pr3+ doped inorganic crystals" IEEE Trans. Nuc. Sci., vol. 40, No. 4, pp. 388-394 (Aug. 1993).*

(Continued)

*Primary Examiner*—Constantine Hannaher
(74) *Attorney, Agent, or Firm*—Ann M. Agosti; Patrick K. Patnode (57) ABSTRACT

A system for use in oil drilling applications includes a scintillator material having a cubic garnet host and praseodymium distributed within the host. The scintillator material emits ultraviolet radiation in response to stimulating gamma ray radiation. A radiation detector optically coupled to the scintillator detects the emitted ultraviolet radiation. In a method for detecting oil, a radiation detector is optically coupled to a scintillator material having a cubic garnet host and praseodymium distributed within the host, wherein the praseodymium acts as an activator, and wherein the scintillator material emits ultraviolet radiation in response to stimulating gamma ray radiation. The detector and the scintillator material are lowered below the surface of the earth, and ultraviolet radiation emitted by the scintillator material in response to stimulating gamma ray radiation reflected by hydrogen bearing compounds indicating the presence of oil is detected by the detector.

20 Claims, 5 Drawing Sheets

OTHER PUBLICATIONS

"The Luminescence of $Pr^3$ in Garnet Phosphors," by D. J. Green et al., Abstract No. 404, *Extended Abstracts*, vol. 85-2, Fall Meeting (Oct. 1985).

W. J. Schipper, et al., "On the Luminescence of Hafnium Compounds", *Mat. Res. Bull,.* vol. 29, pp. 23-30, 1994.

c.Euk, "Fast Scintillators and Their Applications", *Nucl. Tracks Radiat. Meas.*, vol. 21, No. 1, pp 5-10, 1993.

J. A. Mares, et al., "Scintillation and Spectroscopic Properties of $Ce^{3+}$-doped $YAlO_3$ and $Lu_x (RE)_{1-x} AlO_3$ ($RE=Y^{3+}$ and $Gd^{3+}$) Scintillators", *Nuclear Instruments and Methods in Physics Research*, A498, pp. 312-327, Feb. 2003.

C. Blasse, et al., "Fluorescence and Structure of Barium Zirconium Trisilicate", *Journal of Solid State Chemistry*, vol. 2, pp. 105-108, Academic Press, New York and London 1970.

* cited by examiner

ULTRAVIOLET EMITTING SCINTILLATORS FOR OIL DETECTION

BACKGROUND OF THE INVENTION

This invention relates generally to ultraviolet emitting scintillator materials and, more particularly, to an ultraviolet emitting scintillator material for use in environments such as oil well drilling applications.

There is currently a need for gamma ray detection in the oil well drilling industry. High energy gamma rays reflected from Hydrogen (H) bearing compounds underground may indicate specific locations which may have oil. A scintillator material which has high ultraviolet luminescence when activated by gamma rays may be desirable for harsh, down-hole environments where shock levels may be near 250 gravitational acceleration (G) and temperatures may approach or exceed 175° Celsius (C.).

For use in high temperature, harsh environments, the scintillator material may desirably have a number of characteristics. For example, it may be desirable to have a scintillator material which has a sufficient density to absorb as many gamma rays as possible. Second, it may be advantageous for the scintillator material to have a decay time of less than 100 nanoseconds (ns) to limit noise. The scintillator material may also desirably have high transparency in the ultraviolet range, which may be complicated by the number of materials which are opaque in this spectral range. It may also be advantageous for the scintillator material to have low efficiency drop after prolonged exposure to elevated temperatures.

Known detectors utilize ultraviolet scintillator materials but have disadvantages which may prevent them from being used in harsh conditions. In some instances, the scintillator materials' fluorescent decay times may be too long making the scintillator material impractical for use. In other instances, light yield under gamma ray excitation may be poor. Further, light yield may often decrease with increasing temperature. Other scintillator materials' usable life spans may shorten when exposed to high temperatures, with light yield decreasing the longer that exposure to high temperatures continues. Still other materials have emission wavelengths which do not overlap the sensitivity range of a detector used to measure the emitted radiation.

Further complicating the choice of a scintillator material appropriate for harsh environments is the difficulty of predicting which materials will emit ultraviolet radiation in a range which overlaps a radiation detector which is also capable of operating in combination with the scintillator material in harsh, high temperature environments.

These and other drawbacks exist in known systems and techniques.

BRIEF DESCRIPTION OF THE INVENTION

In accordance with an exemplary aspect of the present invention, a system for detection of gamma radiation comprises a scintillator material comprising a cubic garnet host and praseodymium distributed with the host, wherein the praseodymium acts as an activator, and wherein the scintillator material emits ultraviolet radiation in response to the stimulating gamma ray radiation; and a scintillating radiation detector optically coupled to the scintillator material capable of detecting the emitted ultraviolet radiation.

In accordance with another exemplary aspect of the present invention, a method for oil exploration comprises optically coupling a radiation detector to a scintillator material comprising a cubic garnet host and praseodymium distributed within the host, wherein the praseodymium acts as an activator, and wherein the scintillator material emits ultraviolet radiation in response to stimulating gamma ray radiation; lowering the detector and the scintillator material below the surface of the earth; and detecting ultraviolet radiation emitted by the scintillator material in response to stimulating gamma ray radiation reflected by hydrogen bearing compounds indicating the presence of oil.

In accordance with another exemplary aspect of the present invention, a method for detecting gamma ray radiation comprises optically coupling a radiation detector to a scintillator material comprising a cubic garnet host and praseodymium distributed within the host, wherein the praseodymium acts as an activator, and wherein the scintillator material emits ultraviolet radiation in response to stimulating gamma ray radiation; exposing the scintillator material to gamma ray radiation; and detecting with the radiation detector ultraviolet radiation emitted by the scintillator material in response to stimulating gamma ray radiation.

BRIEF DESCRIPTION OF THE DRAWINGS

In order to facilitate a fuller understanding of the present invention, reference is now made to the appended drawings. These drawings should not be construed as limiting the present invention, but are intended to be exemplary only.

DETAILED DESCRIPTION OF EXEMPLARY EMBODIMENTS

An aspect of the present invention is directed to ultraviolet-emitting scintillator materials for use in oil well drilling applications in harsh, down-hole environments where shock levels may be near 250 gravitational acceleration (G) and/or temperatures may approach or exceed 175° C. Another aspect of the invention is directed to an ultraviolet-emitting scintillator material coupled to a radiation detector.

The ultraviolet scintillator material according to exemplary embodiments of the present invention generally has a short decay time and little efficiency drop at elevated temperatures. The ultraviolet scintillator material comprises a cubic garnet host doped with an activator. The scintillator material may be a polycrystalline ceramic formed by sintering phosphors of the scintillator material. Alternatively, the scintillator material may be a single crystal formed from such known techniques as the Czochralski method. Light scattering within the cubic garnet host may be reduced by the cubic crystal structure of the host material.

Garnets are a class of materials with the chemical formula $A_3B_5O_{12}$ in which the A cations are eight coordinated with oxygens and B cations are either six or four coordinated with oxygens. Suitable elements for site A according to exemplary embodiments of the present invention include lutetium (Lu), yttrium (Y), lanthanum (La) and gadolinium (Gd). Suitable elements for site B according to exemplary embodiments of the present invention include aluminum (Al), gallium (Ga), scandium (Sc) and indium (In). Site A may be occupied by one or more elements, such as $Lu_2Y$ for example. Site B may also be occupied by one or more elements, such as $Ga_2Al_3$ for example. In accordance with exemplary embodiments of the present invention, the luminescence activator is preferably praseodymium.

The concentration of the activator is expressed herein in terms of mole percent. Mole percent refers to the mole percent of the activator relative to the A site in the garnet $A_3B_5O_{12}$. For example, 5.0 mole percent praseodymium in lutetium aluminum garnet means that 5 mole percent of the lutetium is replaced with an equal number of moles of praseodymium.

The scintillator material of the present invention may be prepared by reacting source compounds via a flux method using 10% $AlF_3$ flux at about 1450° C. for five hours in a controlled atmosphere to maintain the oxidation state of the activator. Source compounds may include $A_2O_3$, $B_2O_3$ and $Pr_6O_{11}$, for example. The source compounds are preferably 99.99% or higher purity to reduce unknown/uncontrolled impurities in the final composition which can effect radiation damage and quantum efficiency.

A $Pr^{3+}$-activated garnet material may be made by mixing stoichiometric amounts of oxygen-containing compounds of praseodymium, oxygen-containing compounds of at least one rare-earth metal selected from the group consisting of Gd, Y, La and Lu and oxygen-containing compounds of at least one member selected from the group consisting of Al, Sc, Ga, and In. Typically, at least one fluxing compound such as fluorides of praseodymium, lutetium, aluminum, gallium, of indium are added to the mixture in a quantity sufficient to act as a flux. The mixture is then fired in a reducing atmosphere at a temperature and for a time sufficient to convert the mixture to a rare earth-activated garnet phosphor. The fluxing agent may be added before or during the mixing.

The oxygen-containing compounds may be mixed together by any mechanical method including, but not limited to, stirring or blending in a high-speed blender or a ribbon blender. The oxygen-containing compounds may be combined and pulverized together in a bowl mill, a hammer mill, or a jet mill. Wet milling may also carry out the mixing. If the mixture is wet, it may be dried first before being fired under a reducing atmosphere at a temperature from about 900° C. to about 1700° C., preferably from about 1000° C. to about 1600° C., more preferably from about 1200° C. to about 1500° C. for a time sufficient to convert all of the mixture to the final garnet composition. The firing may be conducted in a batchwise or continuous process, preferably with a stirring or mixing action to promote good gas-solid contact. The firing time depends on the quantity of the mixture to be fired, the rate of gas conducted through the firing equipment, and the quality of the gas-solid contact in the firing equipment. Typically, a firing time up to about 10 hours is adequate. The reducing atmosphere typically comprises a reducing gas such as hydrogen, carbon monoxide, or a combination thereof, optionally diluted with an inert gas, such as nitrogen, helium, neon, argon, krypton, xenon, or a combination thereof. Alternatively, the mixture may be packed with high-purity carbon particles in the firing furnace so that the carbon particles react with the oxygen of the oxygen-containing compounds, thereby, generating carbon monoxide that is needed to provide the reducing atmosphere.

Samples of $(Lu_3Al_5O_{12})$:$Pr3^+$ (LAG) were prepared according to the described method from starting materials of $Lu_2O_3$, $Al_2O_3$ and $Pr_6O_{11}$. The mole percent of praseodymium in the LAG ranged from 0.1 to 5.0. During the firing, particles of a coconut charcoal were introduced in a crucible that contained the starting mixture, and the combined assembly was fired at 1450° C. for 5 hours in air. At the end of 5 hours, the solid was cooled at the natural furnace cooling rate. The final phosphor was found to have the required garnet composition.

Figure 1:
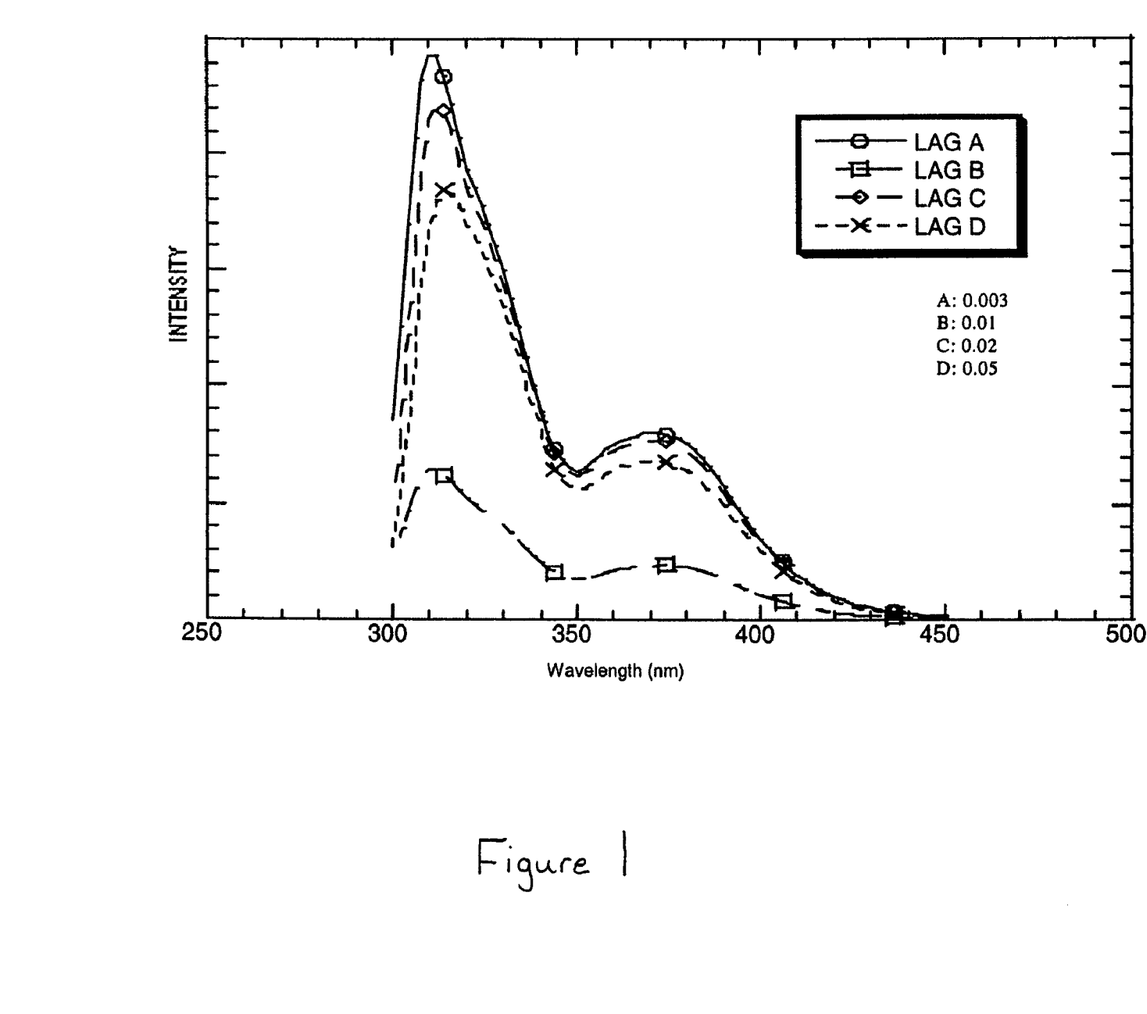
FIG. 1 is a scintillating radiation spectra of $Lu_3Al_5O_{12}$ with varying mole percent of $Pr^{3+}$.

These samples were then exposed to x-ray radiation to characterize ultraviolet emitting properties of the scintillator material when exposed to x-ray or gamma ray radiation. FIG. 1 shows an emission spectrum of the sintered LAG containing varying concentrations of $Pr^{3+}$ activator. Highest intensities of emitted ultraviolet radiation occurred when praseodymium concentration was 0.5 mol %. The spectrum is consistent with a transition of electrons from the 4f5d state to the ground states $^3H_4$, $^3H_5$, and $^3H_6$.

Results of the scintillator material exposed to x-ray radiation are compared against commercially available reference materials in Table 1. Tests were 3+conducted on the sintered LAG sample having 0.5 mol % $Pr^{3+}$.

TABLE 1

| Compound | Peak wavelength (nm) | Primary decay (ns) | Stopping power at 511 keV ($cm^{-1}$) | Change in Light Yield: 150–175° C. (%) |
|---|---|---|---|---|
| $Lu_3Al_5O_{12}$:$Pr^{3+}$ | 310/320/375 | 19 | 0.74 | −20 |
| $BaF_2$ | 310 | 630 | 0.45 | −75 |
| $BaF_2$:$Ce^{3+}$ | 310/325 | 60 | 0.45 | |
| CsI | 305 | 20 | 0.55 | |
| $CeF_3$ | 310/340 | 27 | 0.43 | |
| $Li2HfO3$ | 330/420/610 | | 0.75 | −80 |
| $BaHfSi3O3$ | 450 | | 0.45 | +70 |
| $LiAlO_3$:$Ce^{3+}$ | 365 | 17 | 0.95 | |
| NaI:Tl | 410 | 230 | 0.34 | −50 |

As Table 1 shows, the reference materials do not exhibit the combined properties of short peak wavelength, short primary decay, high stopping power, and low change in light yield at elevated temperatures. Peak wavelengths of the scintillator are typically chosen to overlap the sensitivity for a radiation detector, with a wavelength between about 250 and 450 nm, more typically about 250 to about 350 nm, according to one embodiment.

Alternatively, single crystals of praseodymium doped garnet host may be prepared by the Czochralski method. This known method of crystal growth is accomplished by placing source materials in a high temperature crucible, such as an iridium crucible. The source materials are heated to a temperature above the melting point of the desired crystalline material. This molten material is known as the melt. During growth of the crystal, the melt temperature is held at a value at which an upper portion of the melt is cool enough for a single crystalline material to grow on a seed crystal brought into contact with the melt, but hot enough not to spontaneously nucleate. The seed crystal is then pulled upwards from the melt forming a single crystalline boule.

Single crystalline boules of $Pr^{3+}$ doped $Lu_3Al_5O_{12}$ were grown by the Czochralski method under standard growth conditions for garnet crystals. Source materials for the single crystals were lutetium oxide, aluminum oxide, and praseodymium oxide. Three crystals were grown ranging from 1 to 9 mol % of praseodymium in the melt.

The single crystalline samples of scintillator material were also exposed to x-ray radiation to determine certain properties of the single crystals in the same way as the sintered materials were. Even as temperature increased from room temperature to 175° C., light output decreased only slightly. Measured primary decay and peak wavelength of the single crystals when exposed to the x-ray radiation substantially corresponded to the values measured with the polycrystalline ceramic scintillator material: a 19 ns primary decay time and a peak wavelength at 310 nm.

TABLE 2

| Compound | Change in Light Yield: 25–175° C. (%) |
|---|---|
| LAG 1% Pr in melt | −25% |
| LAG 3% Pr in melt | −20% |
| LAG 9% Pr in melt | −18% |

Figure 2:
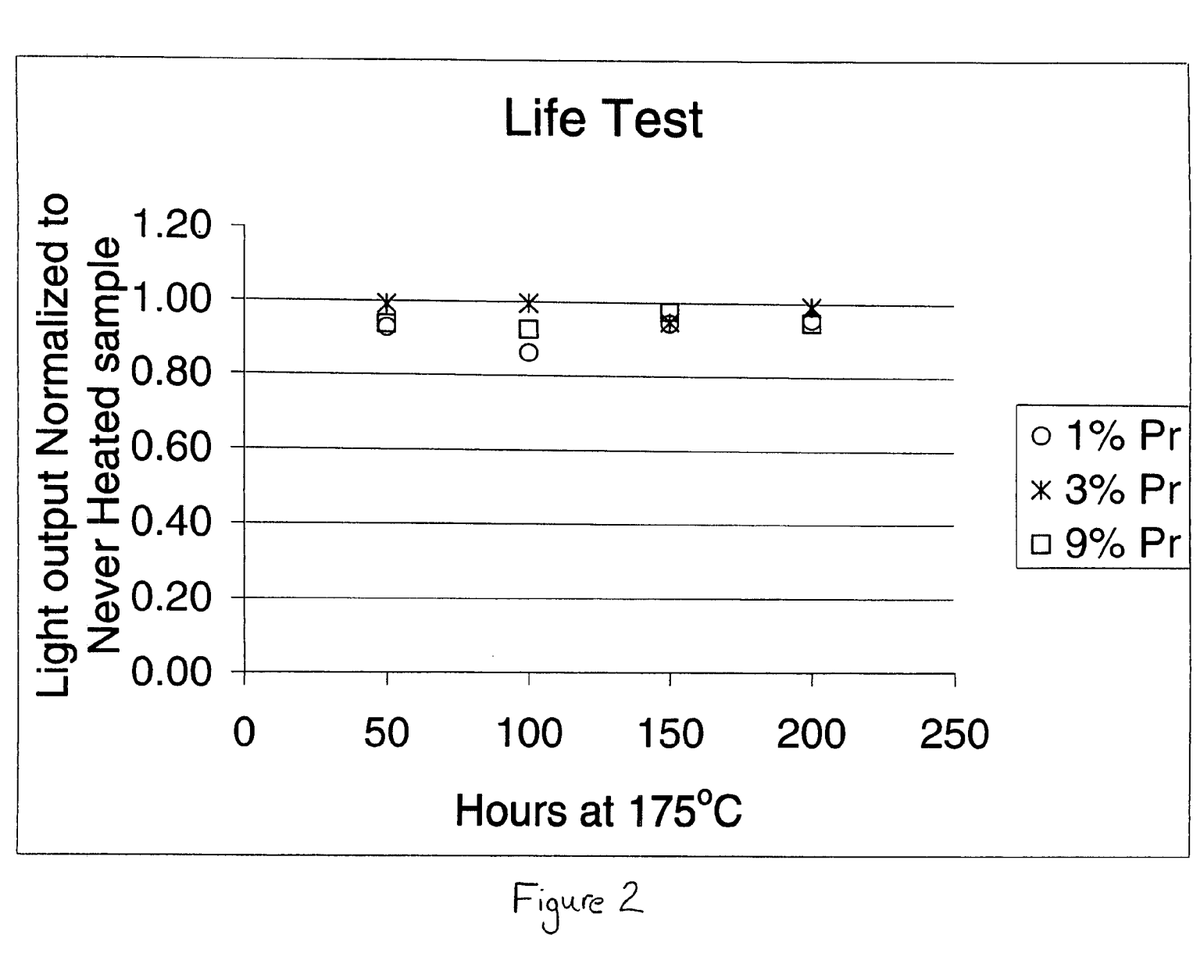
FIG. 2 is a chart showing light yield of single crystals of $Pr^{3+}$ doped $Lu_3Al_5O_{12}$ as a function of time during exposure to elevated temperature.

These samples were then maintained at an elevated temperature of 175° C. for 200 hours. As shown in FIG. 2, even after prolonged periods at elevated temperatures, light yield remained essentially constant, demonstrating the scintillator material's ability to withstand extended lengths of time in harsh, high temperature environments such as in down hole oil drilling applications, for example.

The single crystal samples were also exposed to gamma-ray radiation to measure light yield. These results are summarized below in Table 3, and demonstrate a high transparency of the single crystals in the ultraviolet spectral region.

TABLE 3

| LAG-Single Crystal mol % Pr in melt | Light Yield (photons/MeV) |
|---|---|
| 1 | 7,500 |
| 9 | 10,500 |

Various detectors may be used to measure ultraviolet radiation emitted by a scintillator material such as photomultiplier tubes (PMTs) and avalanche photodiodes (APDs). APDs are typically high-speed, high sensitivity photodiodes utilizing an internal gain mechanism that functions by applying a reverse voltage. Compared to PIN photodiodes, APDs can typically measure even lower level light and are used in a wide variety of applications requiring high sensitivity.

APDs are useful as radiation detectors in harsh, high temperature environments. The APD may be constructed of SiC materials. APDs constructed of these materials generally have a sensitivity range of between about 250 to about 350 nm. An APD is a photodiode that operates with a reverse bias voltage that causes a primary photocurrent to undergo amplification by cumulative multiplication of charge carriers. As the reverse-bias voltage increases toward a breakdown, hole-electron pairs are created by absorbed photons. An avalanche effect occurs when the hole-electron pairs acquire sufficient energy to create additional pairs of holes and electrons, thereby achieving a signal gain.

Epitaxial layers of specific qualities (e.g., doping and thickness) determine operating characteristics (e.g., an avalanche voltage) of devices (e.g., photodiodes) as well as the gain. Ionization coefficients in 4 H, which is a specific crystalline phase of SiC, have a positive temperature coefficient, which may be particularly attractive for a SiC photodiode due to the ionization in an avalanche process. 4 H SiC is a material with a wide band gap (~3.2 eV) and a robust chemical nature. This material can absorb ultraviolet light rays, such as are produced by the described scintillator materials. Due at least in part to the wide band gap, the device used in an embodiment of the present invention may operate at high temperatures. The device further uses a p-n junction, via the n-type epitaxial layers and the p-type substrate. This may be a location for avalanche once a high reverse bias has been applied to the device.

The APD device may include a silicon dioxide ($SiO_2$) passivation layer for providing surface passivation. This $SiO_2$ layer may also serve as an anti-reflection coating, thereby increasing light collection efficiency and overall detection efficiency of the APD device. In addition, a phosphorous silicate glass (PSG) layer may be deposited on the device to control electrical properties otherwise affected by mobile ions. For example, a PSG layer may be provided to prevent mobile ions from moving throughout the device and lowering device performance. Protective layers of $SiO_2$ and PSG provide surface passivation and mobile ion trapping, allowing faster and more efficient device operation while extending the lifetime of the device. In addition, methods for metallization may be used to provide low resistance contacts.

Figure 3:
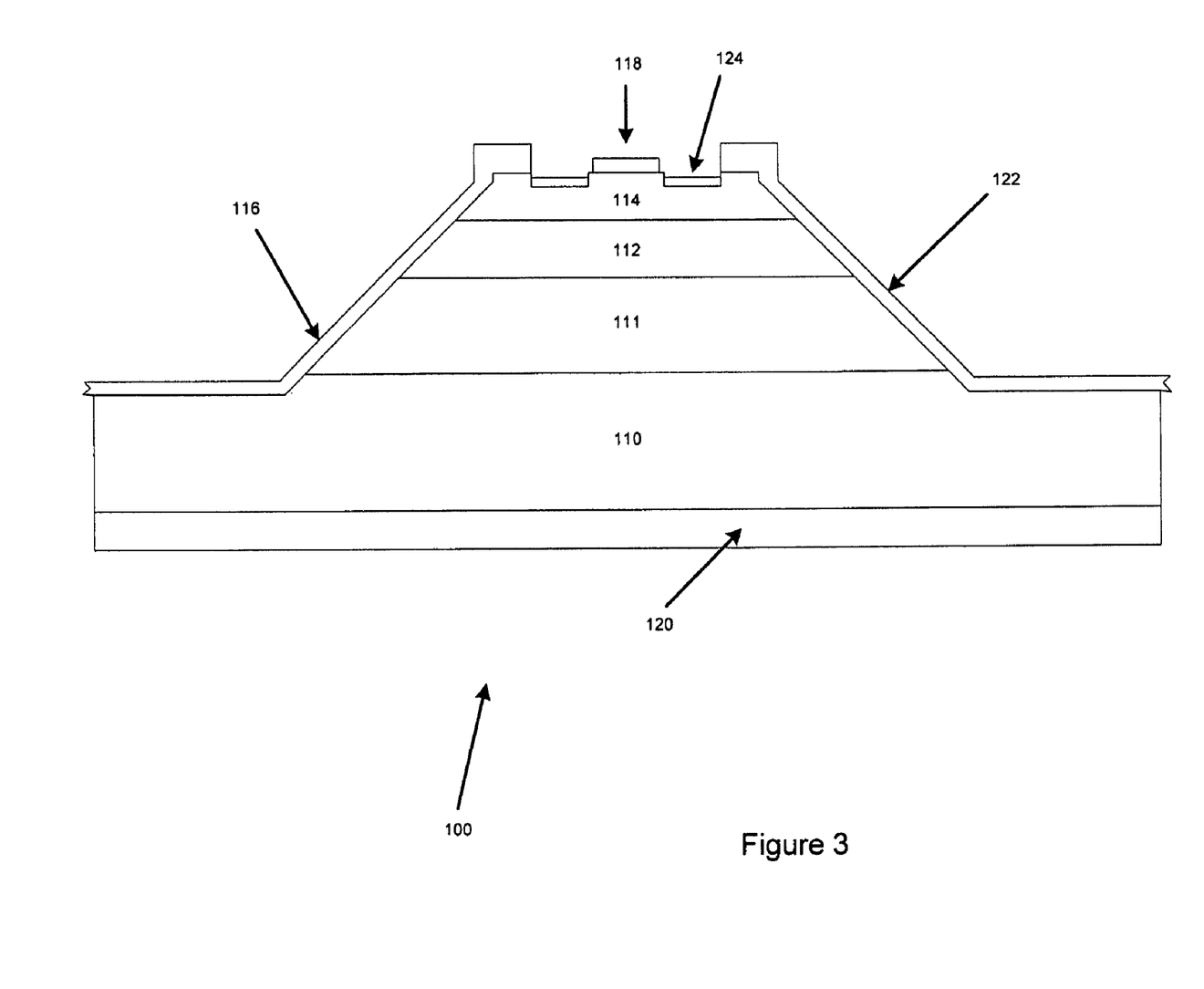
FIG. 3 is an exemplary radiation detector for use in an exemplary embodiment of a system for detecting oil.

FIG. 3 is an example of a cross sectional view of an avalanche photodiode device in accordance with an embodiment of the present invention. FIG. 3 shows a cross-section of the APD device with a substrate 110, a first epitaxial layer 111, a second epitaxial layer 112 and a third epitaxial layer 114. The doped substrate 110 serves to provide electrical contact through an anode of the device. The plurality of epitaxial layers may be grown on the substrate for the formation of a desired electric field profile as a function of depth in the material. The first epitaxial layer 111 may serve to terminate defects at a substrate/epitaxial layers interface as well as form a p-n junction. The second epitaxial layer 112 may serve to allow for a relatively large penetration depth of ultraviolet photons, thereby increasing a probability for absorption and carrier generation events. The third epitaxial layer 114 may provide a low resistance contact to a cathode. This configuration may also serve to confine a high electrical field away from a surface of the device and near the p-n junction and further control a field profile.

The substrate 110 may include a p-doped 4 H SiC substrate, the first epitaxial layer 111 may include a p-doped 4 H SiC layer, the second epitaxial layer 112 may include an n-doped 4 H SiC layer and the third epitaxial layer 114 may include an n-doped SiC layer. More specifically, dopant concentration for substrate 110 may be approximately $5e18$ $cm^{-3}$; dopant concentration for the first epitaxial layer 111 may be approximately $1e17$ $cm^{-3}$, dopant concentration for second epitaxial layer 112 may be approximately $5e16$ $cm^{-3}$ to $6e16$ $cm^{-3}$; and dopant concentration for second epitaxial layer 114 may be approximately $5e18$ $cm^{-3}$. The first epitaxial layer 111 may have a thickness of approximately 1.5 microns, the second epitaxial layer 112 may have a thickness of approximately 3 microns and the third epitaxial layer 114 may have a thickness of approximately 0.4 microns. Other measurements may be implemented as well. For example, the first epitaxial layer 111 may have a thickness of 0.2 to 5 microns with a preferred range of 1 to 2 microns. The second epitaxial layer 112 may have a thickness to facilitate absorption and may range from 2 to 10 microns with a preferred range of 3 to 5 microns. The third epitaxial layer 114 may have a thickness of 0.1 to 2 microns with a preferred range of 0.3 to 0.8 microns.

Metal electrodes 118 and 120 may comprise a combination of various metals. In particular, metal electrode 118 may include Ni/Ti/Mo/Au at a cathode end. Metal electrode 120 may include Al/Ti/Pt/Au at an anode end. Thin metal layers may be used to form electrodes to both p and n contacts while maintaining a low resistance and minimizing or eliminating a drop in electric field. Other materials providing an ohmic contact may be used. Passivation layers 116 and 122 may comprise $SiO_2$, which may have a thickness of 100 Angstroms to several microns (e.g., approximately 5 microns) with a preferred thickness between 1000 Angstroms to 2 microns. In addition, a PSG layer 124 may be implemented to prevent mobile ions from damaging material near the surface and to reduce ultraviolet surface reflection. The PSG layer may have a thickness of approximately 300 Angstroms to 1 micron. Other materials and thickness ranges may be implemented.

The SiC materials may be processed using a dry ion based etching technique, resulting in a sloped mesa sidewall. For example, a photoresist, ion etch process and/or a Fluorine-based chemistry may be used to form sloped sidewall mesas of the APD device. The sloped mesa shape allows a high electrical field of the APD device to be confined to a center of the device, thereby making an avalanche mechanism scalable with area. In other words, the use of a sloped mesa sidewall for electrical field confinement enables the device to be scaled to different sizes for more or less active area. This is particularly advantageous for concentrating the highest electrical field to be within the device, and not at the edges of the device.

An APD device for use in an embodiment of the present invention avalanches uniformly over a collecting area of the device, rather than at the device edges. A positive beveled junction of the present invention stretches the electric field out at the bevel edges but not along a uniform planar portion of a p-n junction. As a result, the highest electric field and therefore the avalanche operation occurs in an active area of the device and not along its periphery. As a result, power dissipated during the avalanche operation is spread across a widest possible area thereby avoiding hot spot formation and associated reliability problems. The third epitaxial layer 114 may serve to prevent higher electric fields from reaching a surface through internal manipulation of a depletion region. This device implements a p-n junction at high applied voltages to initialize an electrical avalanche (e.g., breakdown), near an intended operation point of the device. The electrical field in this type of device may be on the order of a few MeV/cm, supported by a depletion region internal to the device and produced by a large external bias. This device takes advantage of the robust chemical nature of SiC materials and its epitaxial layers, to operate at high temperatures (e.g., 150° C. to 200° C.) and/or high vibrations (e.g., 250 G).

In a separate absorption and multiplication region (SAMR) device, an additional layer may be incorporated between first epitaxial layer 111 and second epitaxial layer 112 wherein the additional layer may be approximately 1.0 micron thick and have an N-dopant concentration of approximately $1e17$ $cm^{-3}$. This may serve to keep a multiplication region centered around the p-n junction (e.g., where the electric field is highest) apart from an absorption region (e.g., second epitaxial layer 112). This may also help to reduce noise observed in the device by minimizing a random absorption phenomena in the multiplication region.

The avalanche aspect of the exemplary APD device may pose an additional constraint, specifically on the angle of the mesa sidewall. As large electrical fields are required in SiC breakdown and therefore avalanche (e.g., typically in the order to 1–3 MV/cm), it is desirable to confine the electrical field away from the edges of the APD device to minimize current leakage occurring at a surface. A sloped mesa may include sidewalls intersecting a substrate by an angle between approximately 20 to 45 degrees. There are currently wet and dry etch techniques for SiC, however, dry etch techniques are more repeatable and controllable in comparison to wet techniques in general.

In dry etching techniques, Reactive Ion Etching (RIE) may be implemented to realize a mesa structure. The effects of the etch may be improved by Inductively Coupled Plasma (ICP), which adds a coil to a standard RIE chamber for additional plasma enhancement. Principally, this involves the generation of additional ions near the material surface, which creates an ion rich plasma and one that is spatially more uniform than RIE plasmas. Results may include improvements in etching control (e.g., physical and chemical) and enhanced uniformity.

Without special treatments to the mask material, the resulting mesa profile may be approximately 0 to 10 degrees variant from the substrate normal, depending on the photoresist (PR) selected and the conditions under which it is treated prior to etching.

There are at least two methods for creating a mesa with a desired angle. The methods may include reflow of the PR and gray scale masking. PR reflow may be performed by hard baking the photoresist following the exposure, allowing solvents to bake out of the PR and letting the surface become "molten," thereby changing the shape of the PR. For example, a photoresist may be used to achieve a target etch depth of approximately 4 microns. The photoresist may afford a coating of thicknesses greater than approximately 10 microns, thereby allowing the target etch depth to be reached with a SiC/PR selectivity as low as 0.5 microns, for example.

Gray scaling takes advantage of a photoresist mask which has been developed in a way to realize several levels of exposure, as determined by transparency or gray scale. Following the exposure through the mask, the photoresist may be developed away, according to a dose of light received through the mask in each area, which may be determined by the transparency of the mask. Thus, the resist may be profiled without heating the resist to a molten state where a desired PR profile may be controllably realized. This profile may be transferred into a semiconductor material as it is etched. The gray scale mask provides a high degree of etching control and repeatability.

Figure 4:
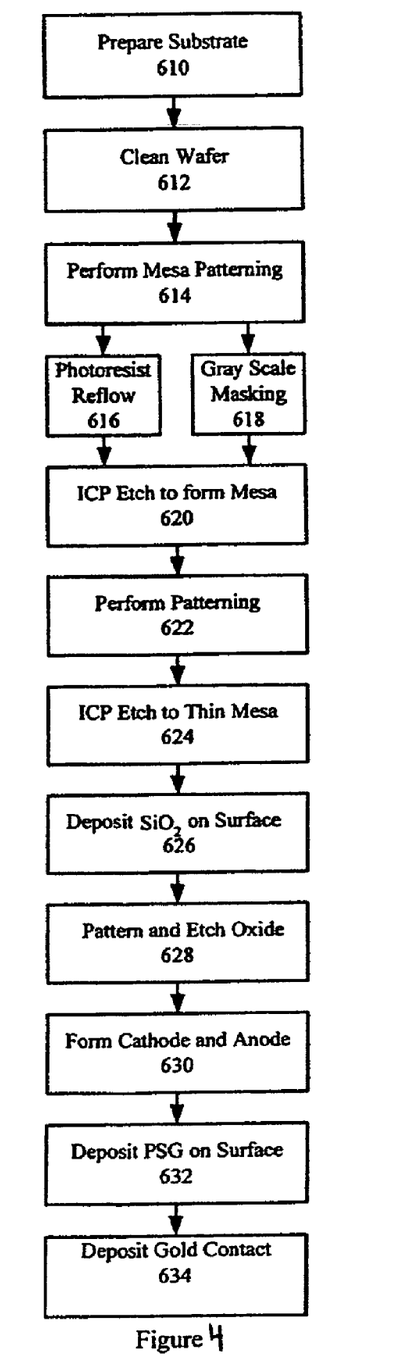
FIG. 4 is a flowchart for making a radiation detector for use in an exemplary embodiment of a system for detecting oil.

FIG. 4 is a flowchart illustrating a method of fabricating APDs for use in an system in accordance with an embodiment of the present invention. At step 610, a substrate is prepared which may include preparing a bulk substrate, for example, and a plurality of epitaxial materials. At step 612, a wafer structure may be cleaned where the wafer structure encompasses the substrate and epitaxial materials of step 610. At step 614, mesa patterning may be performed. Mesa patterning may be formed by a photoresist reflow at step 616 or gray scale masking at step 618. At step 620, ICP etching may be performed to form a mesa structure. At step 622, patterning may be performed. In particular, patterning may refer to a photolithography process in which the photoresist is spun onto the wafer at a controlled speed, aligned with a mask, exposed to high energy light, and developed. The resulting photoresist features may include straight sidewalls with photoresist features near vertical. At step 624, ICP etching may be performed to thin the mesa to a desired thickness. At step 626, a layer of $SiO_2$ may be deposited on a surface of the mesa. At step 628, the $SiO_2$ layer may be patterned and etched to a desired shape and/or thickness. At step 630, a cathode and an anode may be formed. The cathode and anode formation may further involve additional steps of patterning, depositing, liftoff, annealing and/or other additional steps. At step 632, a layer of PSG may be deposited on the surface of the mesa. At step 634, at least one contact (e.g., a gold contact) may be deposited on the structure.

Figure 5:
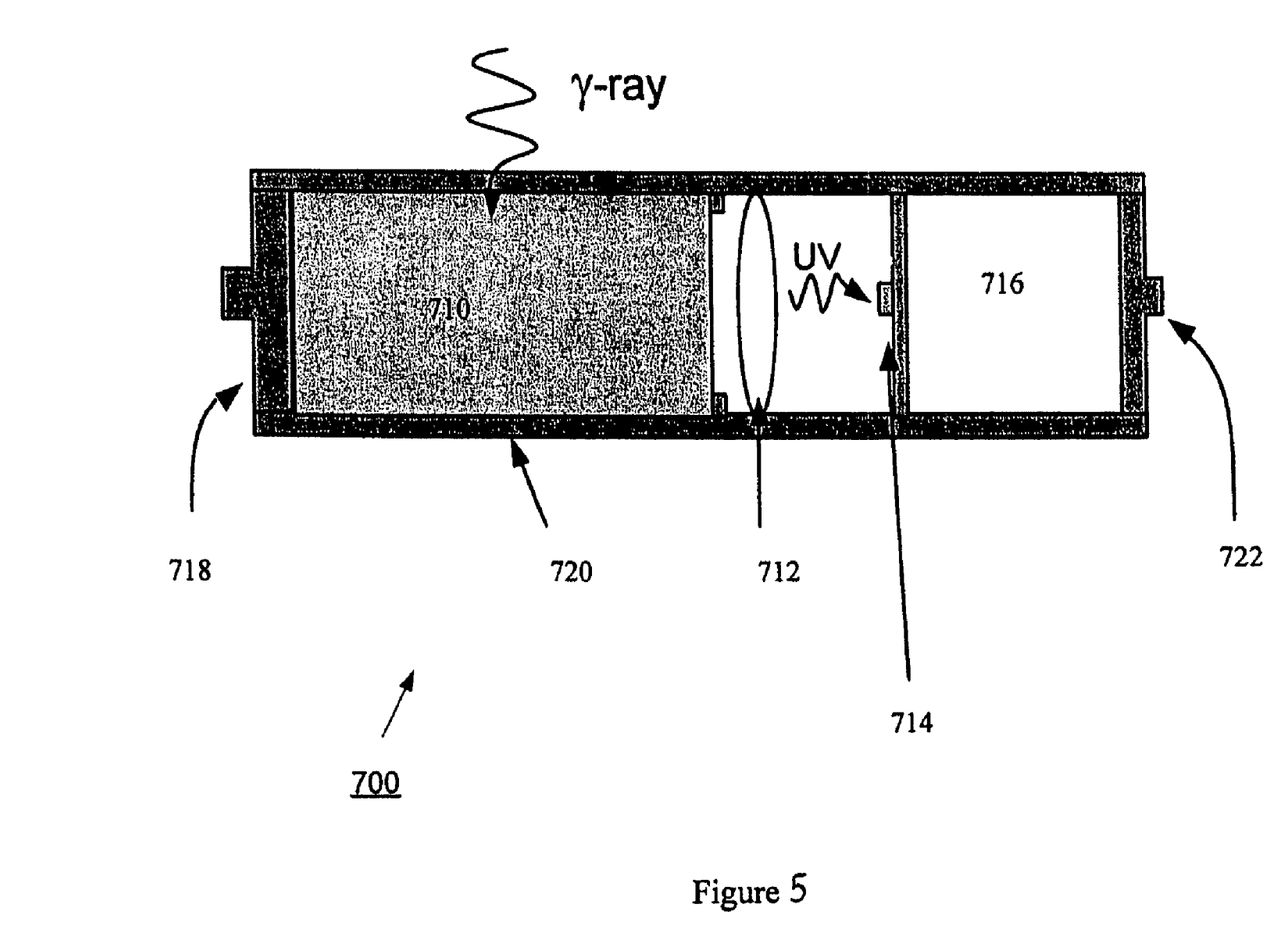
FIG. 5 is an exemplary embodiment of a system for detecting oil.

FIG. 5 is a drawing of an exemplary embodiment of the invention including a scintillator material and a radiation detector. The above features of the SiC APD device may be used with the scintillator materials describe above which convert gamma ray radiation to ultraviolet radiation, observable directly by the SiC APD. A scintillator material as described in detail above may be implemented for detection of gamma rays down-hole in real time. For example, the SiC APD of the present invention may detect ultraviolet light at approximately 250 to 350 nm, such as that produced by the described scintillator materials.

An APD 714 may be used in conjunction with a scintillator material 710 to detect gamma ray radiation. System 700 may include a scintillator material 710 as described above for receiving gamma rays, a lens (or lens structure) 712, APD 714 (e.g., SiC APD) as described in detail above, and amplifier electronics 716. System 700 may also include a compression plate 718, shield 720, and a cable connector 722. System 700 may be cylindrical in shape to facilitate passage of system 700 through a tube.

Scintillator material 710 may receive gamma rays, the energy from gamma rays, such as from H bearing compounds underground, for example, which may cause electrons in the $Pr^{3+}$ to ascend to higher energy levels. The electrons may return to the ground state, causing an emission of an ultraviolet ray. The ultraviolet ray may be focused by lens 712 (or other lens structure) and received by an APD 714, such as a SiC APD. Additional electronics, such as amplifier electronics 716 may be used to enhance, amplify or otherwise manipulate the received ultraviolet signal. These components may be incorporated into a tube for down hole deployment in various applications, such as oil well drilling. The system of FIG. 5 takes advantage of the robust nature of described ultraviolet emitting scintillator materials and a SiC avalanche photodiode, as shown as 714, operable at high temperatures (e.g., 150° C. to 200° C.) and/or high vibrations (e.g., 250 G).

The present invention is not to be limited in scope by the specific embodiments described herein. Indeed, various modifications of the present invention, in addition to those described herein, will be apparent to those of ordinary skill in the art from the foregoing description and accompanying drawings. Thus, such modifications are intended to fall within the scope of the following appended claims. Further, although the present invention has been described herein in the context of a particular implementation in a particular environment for a particular purpose, those of ordinary skill in the art will recognize that its usefulness is not limited thereto and that the present invention can be beneficially implemented in other environments for other purposes. Accordingly, the claims set forth below should be construed in view of the full breath and spirit of the present invention as disclosed herein.

What is claimed is:

1. A system for detection of oil comprising:
   a scintillator material comprising a garnet host with the formula $A_3B_5O_{12}$, wherein A comprises Lu and optionally one or more elements selected from the group consisting of Y, La, and Gd, and wherein B comprises one or more elements selected from the group consisting of Al, GA, Sc, and In and praseodymium distributed within the host, wherein the praseodymium acts as an activator, and wherein the scintillator emits ultraviolet radiation in response to stimulating gamma ray radiation; and
   a scintillating radiation detector optically coupled to the scintillator capable of detecting the emitted ultraviolet radiation.

2. The system of claim 1, wherein the scintillator material has a primary decay time of less than about 20 nanoseconds.

3. The system of claim 1, wherein the stimulating gamma ray radiation is reflected by hydrogen bearing compounds indicating the presence of oil.

4. The system of claim 3, wherein the praseodymium is present in the range of about 0.01 mole percent to about 9 mole percent relative to element A.

5. The system of claim 1, wherein B comprises Al.

6. The system of claim 1, wherein the detector is an avalanche photodiode.

7. The system of claim 6, wherein the avalanche photodiode is a SiC avalanche photodiode.

8. The system of claim 1 wherein the system is capable of operating at temperatures up to about 175° C.

9. The system of claim 1 further comprising a lens for focusing the emitted radiation on the radiation detector.

10. The system of claim 1 further comprising an amplifier.

11. The system of claim 1 wherein the scintillator material is a single crystal.

12. The system of claim 11 wherein the scintillator material is a single crystal having the formula $(Lu_3Al_5O_{12}):Pr^{3+}$.

13. A method for oil exploration comprising:
    optically coupling a radiation detector to a scintillator material comprising a garnet host with the formula $A_3B_5O_{12}$, wherein A comprises Lu and optionally one or more elements selected from the group consisting of Y, La, and Gd, and wherein B comprises one or more elements selected from the group consisting of Al, GA, Sc, and In and praseodymium distributed within the host, wherein the praseodymium acts as an activator, and wherein the scintillator material emits ultraviolet radiation in response to stimulating gamma ray radiation;
    lowering the detector and the scintillator material below the surface of the earth;
    detecting ultraviolet radiation emitted by the scintillator material in response to stimulating gamma ray radiation reflected by hydrogen bearing compounds indicating the presence of oil.

14. A method for detecting gamma ray radiation comprising:
    optically coupling a radiation detector to a scintillator material comprising a garnet host with the formula $A_3B_5O_{12}$, wherein A comprises Lu and optionally one or more elements selected from the group consisting of Y, La, and Gd, and wherein B comprises one or more elements selected from the group consisting of Al, GA, Sc, and In and praseodymium distributed within the host, wherein the praseodymium acts as an activator, and wherein the scintillator material emits ultraviolet radiation in response to stimulating gamma ray radiation;

exposing the scintillator material to gamma ray radiation;

detecting with the radiation detector ultraviolet radiation emitted by the scintillator material in response to stimulating gamma ray radiation.

15. The method of claim 14 wherein B comprises Al.

16. The method of claim 15, wherein the praseodymium is present in the range of about 0.01 mole percent to about 9 mole percent relative to element A.

17. The method of claim 14 wherein the scintillator material is a single crystal.

18. The method of claims 17 wherein the scintillator material is a single crystal having the formula $(Lu_3Al_5O_{12}):Pr^{3+}$.

19. The method of claim 18 wherein the praseodymium is present in the range of about 0.01 mole percent to about 9 mole percent relative to Lu.

20. A scintillator material comprising a mixed garnet host with the formula $(Lu_{1-x}A_x)_3Al_5O_{12}$, where $A=Y^{3+}$, $La^{3+}$ and $Gd^{3+}$ and $0<x<0.99$ and praseodymium as an activator, wherein the scintillator emits ultraviolet radiation in response to stimulating gamma ray radiation.

* * * * *